United States Patent
Melzi et al.

(10) Patent No.: US 7,271,589 B2
(45) Date of Patent: Sep. 18, 2007

(54) PROBE HEAD FOR NUCLEAR MAGNETIC RESONANCE MEASUREMENTS

(75) Inventors: Roberto Melzi, Concorezzo (IT); Fabio Tedoldi, Pavia (IT); Giovanni Bizzaro, Milan (IT)

(73) Assignee: Bruker BioSpin GmbH, Rheinstetten-Forchheim (DE)

( * ) Notice: Subject to any disclaimer, the term of this patent is extended or adjusted under 35 U.S.C. 154(b) by 0 days.

(21) Appl. No.: 11/440,411

(22) Filed: May 24, 2006

(65) Prior Publication Data

US 2006/0290352 A1    Dec. 28, 2006

(30) Foreign Application Priority Data

May 24, 2005   (DE)   ............ 10 2005 024 479

(51) Int. Cl.
*G01V 3/00* (2006.01)
(52) U.S. Cl. ..................... 324/318; 324/322
(58) Field of Classification Search ............. 324/318, 324/322
See application file for complete search history.

(56) References Cited

U.S. PATENT DOCUMENTS

| | | | | |
|---|---|---|---|---|
| 5,959,454 | A * | 9/1999 | Westphal et al. | 324/320 |
| 6,091,241 | A * | 7/2000 | Querleux et al. | 324/300 |
| 6,366,093 | B1 * | 4/2002 | Hartman | 324/318 |
| 6,977,503 | B2 * | 12/2005 | Prado | 324/319 |
| 2002/0084783 | A1 | 7/2002 | Blumich et al. | |
| 2002/0089330 | A1 | 7/2002 | Blumich et al. | |

FOREIGN PATENT DOCUMENTS

WO   WO 2004/061468 A1   7/2004

OTHER PUBLICATIONS

Balibanu, et al., Nuclear Magnetic Resonance in Inhomogeneous Magnetic Fields:. J. Magn. Res., 145, 2000, pp. 246-258.
Hürlimann, J. "Car-Purcell Sequences with Composite Pulses", Magn. Res., 152, 2001, pp. 109-123.
Casanova, et al., "Two-Dimensional Imaging with a Single-Sided NMR Probe", J. Magn. Res., 163, 2003, pp. 38-45.
"Spectroscopy-NOW/Reasonants", 8, 2005, John Wiley & Sons (www.spectroscopynow.com/Spy/basehtml/SpyH/1,1181,5-5-7-0-89587-ezine-0-2,00.html).
Brown, et al., "Surface Normal Imaging with a Hand-Held NMR Device", J. Magn. Res., 169, 2004, pp. 308-3012.

* cited by examiner

*Primary Examiner*—Louis M. Arana
(74) *Attorney, Agent, or Firm*—Law Offices of Paul E. Kudirka

(57) ABSTRACT

A probe head for nuclear magnetic resonance measurements in an area of a surface of a measuring object is disclosed. The probe head comprises first means for generating a static magnetic field extending at least partially parallel to the surface, second means for generating a radio frequency magnetic field having components extending perpendicular to the surface, and third means for amplifying a radio frequency magnetic field effective within the measuring object. The third means are configured as an aperture and are located between the second means and the surface.

16 Claims, 5 Drawing Sheets

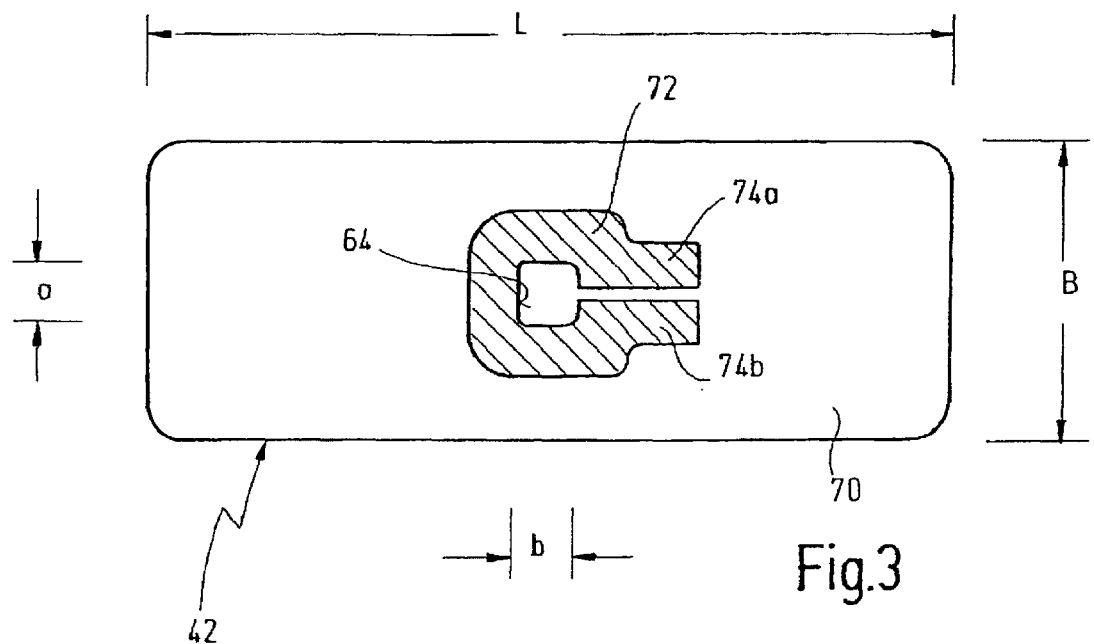
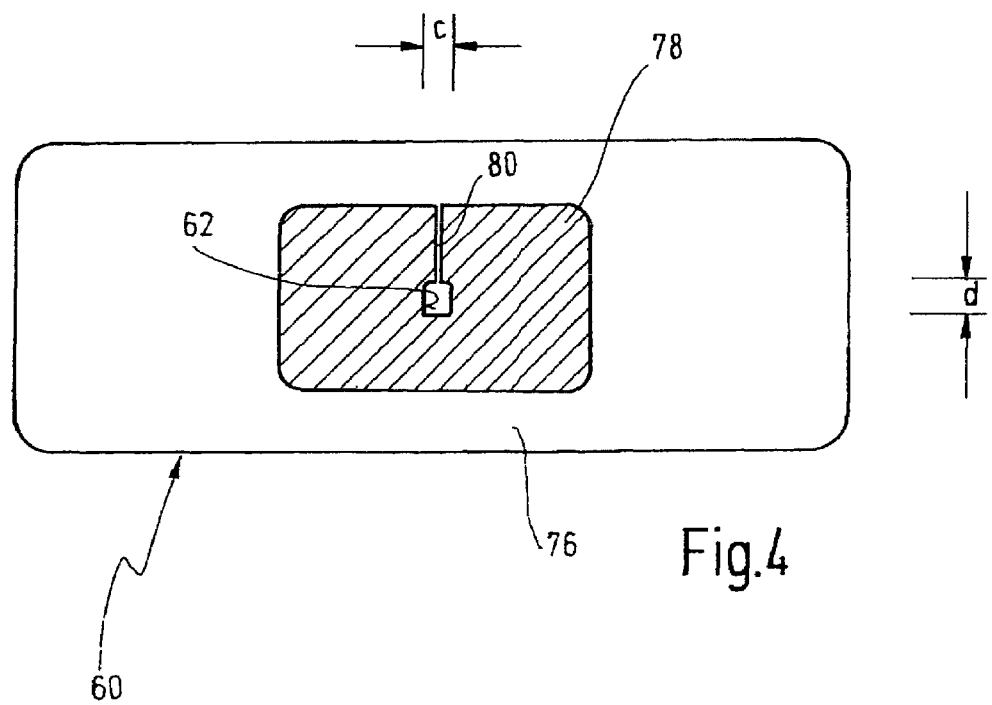

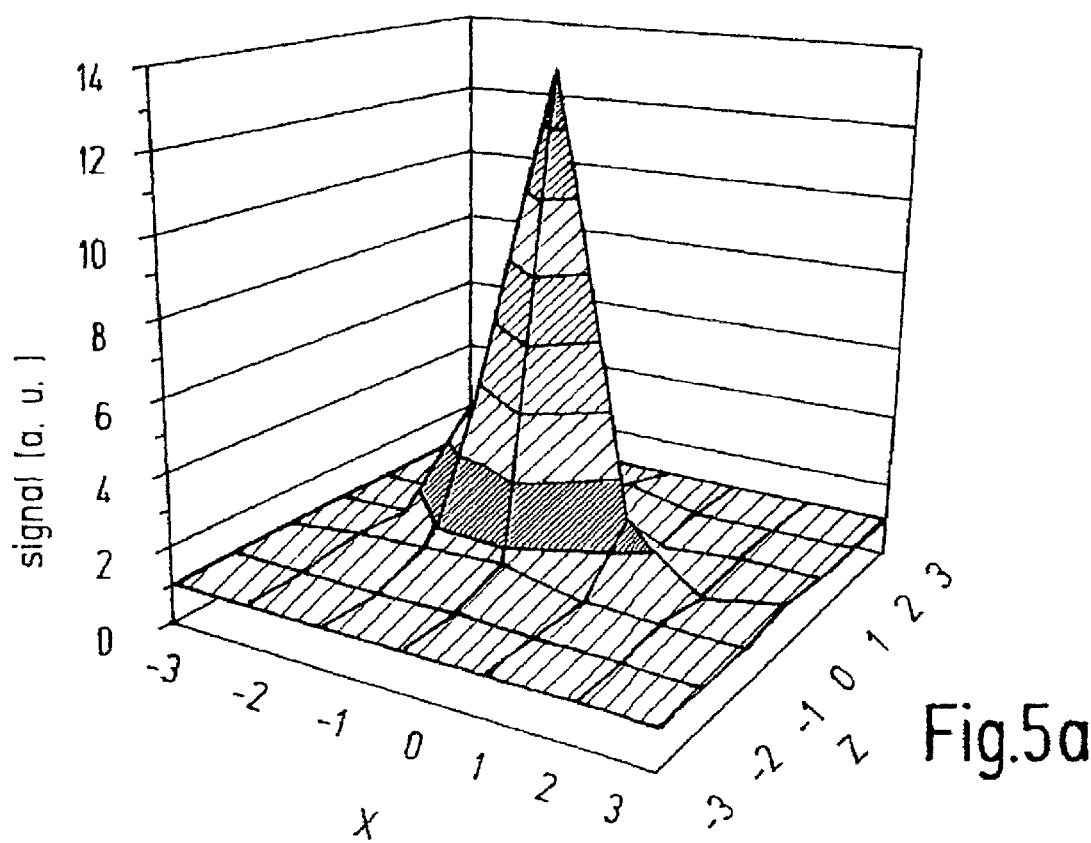

PROBE HEAD FOR NUCLEAR MAGNETIC RESONANCE MEASUREMENTS

FIELD OF THE INVENTION

The invention, generally, is related to the field of nuclear magnetic resonance (NMR) measurements.

More specifically, the invention is related to the field of probe heads for such measurements, in particular to the field of so-called surface coil probe heads.

Still more specifically, the invention is related to a probe head for nuclear magnetic resonance measurements in the area of a surface of a measuring object, comprising first means for generating a static magnetic field extending at least partially parallel to the surface, second means for generating a radio frequency magnetic field having components extending perpendicular to the surface, and third means for amplifying the radio frequency magnetic field effective within the measuring object.

BACKGROUND OF THE INVENTION

For investigating areas of objects which are close to the object's surface it is well known in the art of NMR to use so-called surface coils. An example for such a coil is disclosed in US Patent Application Publications 2002/0089330 A1 and 2002/0084783 A1. These devices, having commercially become known under the trade name "NMR MOUSE®" utilize a U-shaped magnet system with permanent magnets. In the area of the gap between the magnet poles there exist components of the static magnetic field $B_0$ extending parallel to the surface of the magnets defined by the front surfaces of the magnet poles. In this area between the legs, i.e. within the gap, a radio frequency coil is positioned parallel to the magnet surfaces. The field lines of the radio frequency magnetic field $B_1$ generated by the coil have components extending perpendicular to the static magnetic field $B_0$. The field lines of the static magnetic field $B_0$ and the field lines of the radio frequency magnetic field $B_1$, therefore, intersect in an area above the surface and fulfil the one condition for the excitation of nuclear magnetic resonance and for the reception of nuclear magnetic resonance signals, resp., namely $B_0 \times B_1 \neq 0$. This prior art apparatus operates within a relatively low frequency range of e.g. $v_0 = \omega_0/2\pi = 15$ MHz with $\omega_0 = \gamma B_0$, where $\gamma$ is the so-called gyromagnetic ratio. For such a frequency range the static magnetic field $B_0$ may be generated with permanent magnets.

If this prior art apparatus is placed on a surface of a measuring object under investigation, nuclear magnetic resonance signals may be generated and received in areas close to the surface. This method has been used for various applications like material science, the characterization of elastomers, quality control, for example in the rubber industry, explorative studies for curatorial problems and medical diagnostics.

Conventional apparatuses of this kind are characterized by their relatively limited sensitivity and their limited spatial resolution. As is generally known, the signal-to-noise ratio that may be expected in NMR measurements, depends on the number of nuclear spins contributing to the signal. In the case of the inhomogeneous magnetic fields of the present apparatus, the pulse bandwidth must, therefore, be considered as the decisive factor which, in conjunction with the spatial distribution of the static magnetic field (which is not constant in space) defines the sensitive volume (cf. Balibanu et al., J. Magn. Res., 145, (2000) pp. 246-258; Hürlimann, J. Magn. Res., 152, (2001), pp. 109-123).

The best measurements may, hence, be expected when, on the one hand, destructive interferences of the measuring signals from different sub-volumes of the sample within the sensitive volume are avoided, in which $B_0 \times B_1 \neq 0$ and $\omega_0 = \gamma B_0$, and, on the other hand, the bandwidth of the radio frequency pulses which is linked to the $B_1$ intensity, is large. The $B_1$ intensity and, likewise, the signal-to-noise ratio that may be expected within the stray field of the surface coil, depend superproportionally from the reciprocal value of the distance from the surface.

If, on the other hand, a surface area shall be measured with a high spatial resolution, e.g. in the mm range, then signals from adjacent areas must be suppressed. This may preferably be done by a spatial limitation of the radio frequency field, for example with micro coils. Insofar, the inherent inhomogeneity of the $B_0$ field is helpful.

A common approach for the imaging detection is the realization of spatial resolution by means of additional gradients, as are also used in 2D tomographs (Casanova et al., J. Magn. Res., 163, (2003) pp. 38-45). This approach, however, requires substantial design efforts and results in complex apparatuses which are difficult to operate and are, for example, inappropriate for mobile applications.

In contrast thereto it is much simpler and more cost effective in such cases to use very small coils for achieving a high spatial resolution with a high filling factor and, hence, high sensitivity. For a series resonant circuit, the quality factor Q is proportional to $\omega_0 L/R$, such that a small inductivity L seems to be of little advantage. However, in the field of NMR the quality factor Q does not really set limits at low frequencies because, first, there are known resonant circuit concepts at hand bringing L and R into a range that is acceptable for the experiment, second, there is sufficient power available, and, third, a finite pulse length is necessary for the definition of the carrier frequency $\omega_0$.

In an article "NMR microscope" published in the internet journal "spectroscopy-NOW/Resonants", 8, (2005), John Wiley & Sons (www.spectroscopynow.com/Spy/basehtml/SpyH/1,1181,5-5-7-0-89587-ezine-0-2,00.html) a so-called NMR microscope for medical diagnostic applications is disclosed. This microscope uses a tubular magnet system being configured by a tubular direct current magnet having coils at one terminal end thereof for generating an arc-shaped constant magnetic field $B_0$. A funnel-like radio frequency antenna is positioned within the central longitudinal opening of the magnet system. The antenna consists of a plurality of capacitive/inductive rings of stepped diameter which are arranged at an axial distance with respect to each other. The antenna is tapered in the direction towards the object under investigation. Such an antenna is also disclosed in WO 2004/083883 A1 for a measuring wavelength of 1 m, corresponding to a measuring frequency of 300 MHz. The configuration of the antenna shall effect a focussing of the radio frequency magnetic field $B_1$ into the object under investigation which, for a spatial resolution of 10 µm shall result in an enhancement of the sensitivity by a factor of 100.

This prior art apparatus has the disadvantage that it is complex in its design and has large dimensions. It is, further, dimensioned for a radio frequency range in which the required constant magnetic field $B_0$ may no more be generated by simple permanent magnets but an electromagnet system is required instead. Accordingly, the prior art apparatus may solely be used in a laboratory environment. Mobile field applications, in particular under confined spatial circumstances, are impossible. The conditions underlying conventional NMR within a homogeneous field $B_0$ as disclosed in WO 2004/083883 A1 are, therefore, not transferable to the present invention.

SUMMARY OF THE INVENTION

It is, therefore, an object underlying the invention, to improve a probe head of the type specified at the outset, such that the afore-mentioned disadvantages, in particular those related to technically complicated designs, are avoided. In particular, a probe head design shall be made available having small dimensions, a robust design, a simple operation, and which may be manufactured at low cost.

This object is achieved by the present invention with a probe head for nuclear magnetic resonance measurements in the area of a surface of a measuring object, comprising first means for generating a static magnetic field extending at least partially parallel to the surface, second means for generating a radio frequency magnetic field having components extending perpendicular to the surface, and third means for amplifying the radio frequency magnetic field effective within the measuring object, characterized in that the third means are configured as an aperture and are located between the second means and the surface.

The object underlying the invention is, thus, entirely solved.

The invention provides a probe head with an extremely simple and flat design being based on prior art probe heads with permanent magnet systems as discussed above with reference to US Patent Application Publications 2002/0089330 A1 and 2002/0084783 A1 and which are commercially available in the same design. As compared to these prior art systems only minor modifications are necessary such that the robust and simple design of these prior art apparatuses are preserved. The probe head of the present invention may, therefore be used under the same rough operational conditions in a field, also under confined spatial conditions.

Preferably, the aperture comprises a first opening, and a slot extending away from the first opening.

This measure has the advantage that eddy currents within the aperture are suppressed.

In a preferred embodiment of the invention, the second means are configured as a planar coil.

This measure has the advantage that a flat design is possible.

Insofar, it is particularly preferred when the planar coil is configured as a loop-shaped conductive coating on a first substrate.

This measure has the advantage that the planar coil may be manufactured in a simple technological manner.

The same holds true when the aperture is configured as a planar conductive coating on a second substrate, the coating being provided with the first opening.

In the cases mentioned before a particularly good effect is achieved when the first substrate and the second substrate are configured as one and the same substrate, wherein the planar coil and the aperture are located on opposite surfaces thereof. The distance between the coil and the aperture as well as the dielectric constant of the substrate are of particular importance insofar.

This measure has the advantage that minimum dimensions of the coil and of the aperture may be obtained in a direction perpendicular to the surface of the object under investigation. This extremely flat design guarantees that the measuring objects may be analysed even very close to the surface at relatively high $B_1$ intensities.

In embodiments of the invention, the loop-shaped conductive coating is provided with a second opening being essentially square-shaped, wherein, preferably, the first opening is also essentially square-shaped. It is, insofar, possible, to adapt the geometry to the particular requirements of an investigation or experiment. Modifications of the $B_0$ geometry may likewise be taken into account.

This shape of the openings has turned out to be of particular advantage, considering the conventional $B_0$ field geometry and the spatial resolution to be attained.

It is, further, preferred, when the first and the second openings are arranged coaxially.

Practical tests of embodiments of the probe head according to the present invention have shown that the first and the second opening should have an area ratio in the range of between 1:2 and 1:6, preferably of about 1:4. For example, at a frequency of the radio frequency magnetic field $B_1$ of about 15 MHz the first opening may have dimensions of 2×2 mm and the second opening may have dimensions of 4×4 mm.

In further embodiments of the invention, the first means are configured as a U-shaped magnet system, wherein the second and the third means are located between legs of the U. The magnet system may comprise two legs configured as permanent magnets interconnected by a yoke. Other geometries of the design are, of course, possible depending on the particular requirements of an application, and are within the scope of the present invention.

Preferably, the second means are located within an electrically conductive housing having a side facing the surface, the third means being arranged within the side.

Thereby, the radio frequency assembly is shielded against spurious signals from the environment, and an unwanted coupling with the magnet system, possibly time-varying couplings, are suppressed.

Preferably, means for radio frequency matching and tuning are provided within the housing, which, therefore, are likewise shielded.

This compact and well-defined design allows to maintain a certain setting of the tuning over extended periods of time, wherein the tuning remains unaffected by external influences.

It is possible to provide a plurality of exchangeable housings with second and third means.

By doing so, second and third means of different design and tuning may be used depending on the particular requirements of an application, in particular second and third means having different sensitivities or measuring depths, while the same first means are used.

Further advantages will become apparent from the description and the attached drawing.

It goes without saying that the features mentioned before and those that will be explained hereinafter may not only be used in the particularly given combination but also in other combinations or alone without leaving the scope of the present invention.

BRIEF DESCRIPTION OF THE DRAWINGS

The above and further advantages of the invention may be better understood by referring to the following description in conjunction with the accompanying drawings in which:

FIG. 3 on an enlarged scale shows a top plan view of a planar coil, as may be used for the probe head of FIG. 2;

FIG. 4 on an enlarged scale shows a top plan view of an aperture, as may be used for the probe head of FIG. 2; and shows experimentally obtained two-dimensional spatial dependencies of the measuring signal intensity of a small sample object (1 mm³ natural caoutchouc) in a 1 mm raster within a plane directly adjacent the surface: a) with aperture, and b) without aperture.

FIG. 5a, as an example, shows the experimentally determined two-dimensional spatial dependance of the measuring signal amplitude of a small sample object (1 mm³ natural caoutchouc) in a 1 mm raster within a plane directly at the surface with an aperture;

DETAILED DESCRIPTION

Figure 1:
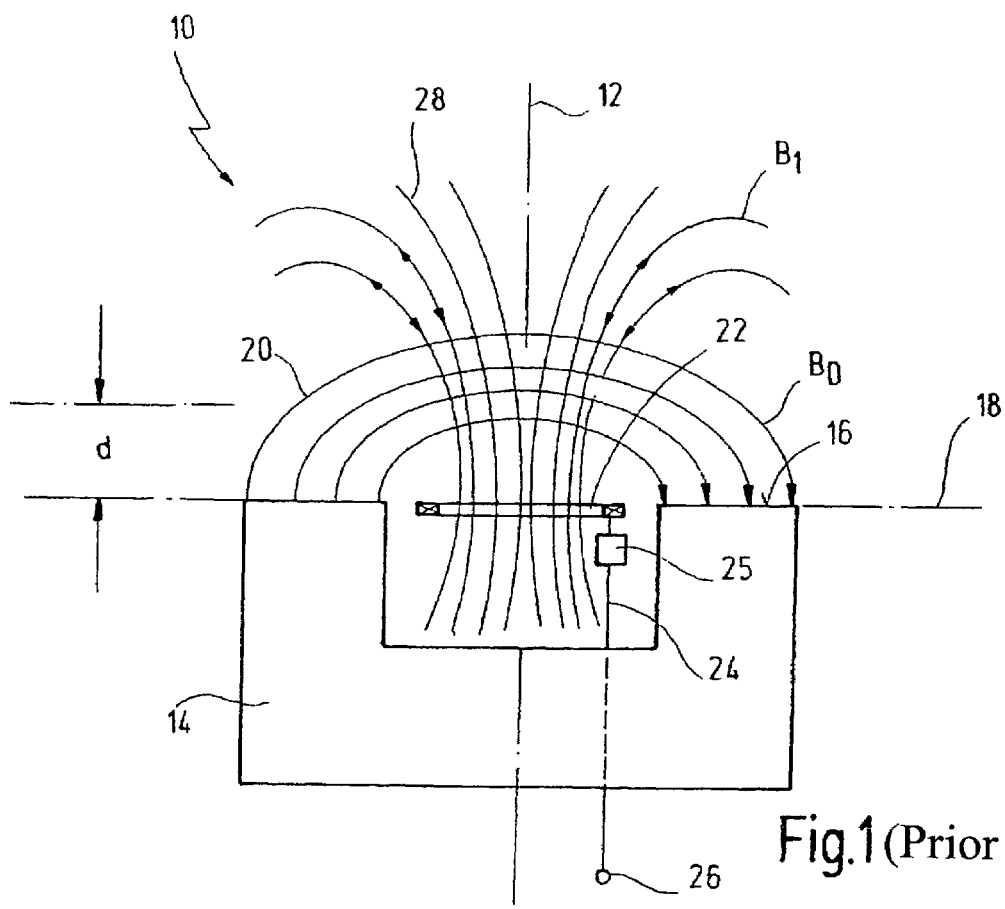
FIG. 1 shows a schematic side elevational view of a probe head according to the prior art.

In FIG. 1 reference numeral 10 as a whole designates a probe head for measurements close to the surface by means of NMR, according to the prior art. A U-shaped magnet system 14 is provided symmetrically to an axis 12. Magnet system 14 has legs having free surfaces which configure contact surfaces 16 of probe head 10. Probe head 10 may be applied with these contact surfaces 16 on a surface 18 of a measuring object, with surface 18 extending perpendicular to axis 12.

Field lines 20 of the constant magnetic field $B_0$ generated by magnet system 14 exit under right angles from contact surfaces 16, and bridge the gap between the legs with an arc. In the area of axis 12 the extend perpendicular to the latter.

A radio frequency coil 22 is located between the legs of magnet system 14 in the area of axis 12. Radio frequency coil 22 is connected to a terminal 26 via a line 24 and a matching and tuning unit 25. Radio frequency coil 24 is positioned such that field lines 28 of a radio frequency magnetic field $B_1$ generated by it extend essentially parallel to axis 12 in the area of surface 18. A limited spatial area close to surface 18 and within the measuring object is thus generated in which field lines 20 of field $B_0$ intersect field lines 28 of field $B_1$ under right angles. In this area the condition for exciting nuclear magnetic resonance and for receiving nuclear magnetic resonance signals, resp., is maximally fulfilled.

Figure 2:
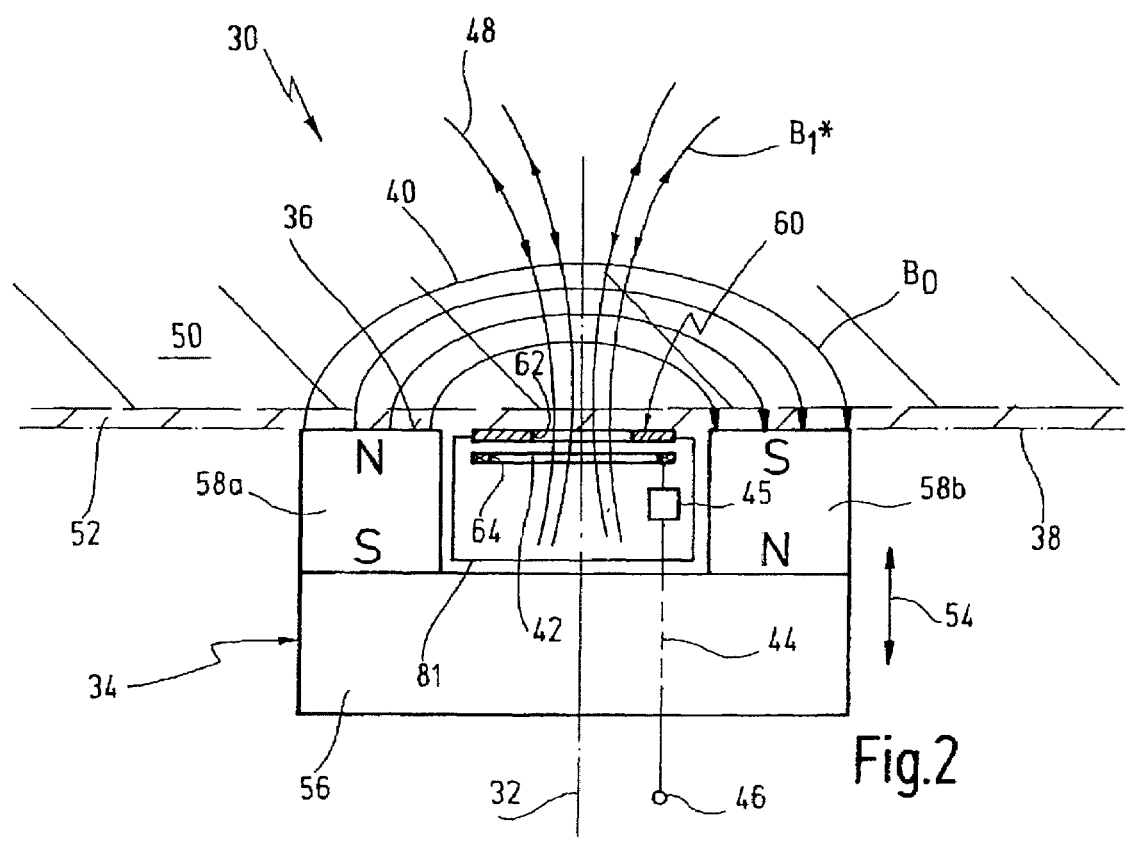
FIG. 2 shows an illustration, similar to that of FIG. 1, however, for an embodiment of the present invention.

FIG. 2 shows an apparatus similar to that of FIG. 1, however, for an embodiment of the present invention.

A probe head 30 with an axis 32 comprises a magnet system 34, contact surfaces 36 of which contact a surface 38 of a measuring object under investigation. The field lines of constant magnetic field $B_0$ generated by magnet system 34 are designated 40. A radio frequency coil 42 is positioned within an electrically conductive housing 81 between legs of magnet system 34, and is connected with a terminal 46 via a line 44 and a matching and tuning unit 45. The field lines of radio frequency field $B_1^*$ generated by coil 42 are designated 48.

In FIG. 2 a brickwork wall structure 50 is shown as an example for a measuring object. Wall structure 50 is provided with a fresco painting 52. Depending on how close probe head 30 is approached to fresco painting 52 (arrow 54) or depending on the particular design of probe head 30, spatially resolved measurements may be made on fresco painting 52 for curatorial purposes.

Magnet system 34 is of a design comprising a yoke 56 made from soft iron and two permanent magnets 58a and 58b of oppositely directed polarity which configure the two legs of magnet system 34.

The main distinction as compared to prior art probe head 10 of FIG. 1 is that probe head 30 has an element between radio frequency coil 42 and surface 38 which modifies field lines 48, i.e. also modifies radio frequency field $B_1^*$. This element is configured as a hole or aperture 60. Aperture 60 has a first opening 62 being smaller than a second opening 64 of radio frequency coil 42. Openings 62 and 64 are preferably arranged coaxially along axis 32.

FIGS. 3 and 4 on an enlarged scale show details of radio frequency coil 42 (FIG. 3) and of aperture 60 (FIG. 4).

In an embodiment of the invention radio frequency coil 42 as well as aperture 60 are located on a substrate 70 and 76, resp., substrates 70 and 76 being, for example, made from the same material as is used for printed circuit boards. Radio frequency coil 42 and aperture 60 are preferably manufactured by appropriately coating substrates 70 and 76. As an alternative, they can be arranged on opposite surfaces of one and the same substrate for achieving a still flatter design.

Radio frequency coil 42 is configured by a loop-shaped, electrically conductive coating 72, for example a copper coating, on substrate 70. Loop-shaped coating 72 ends in two terminals 74a and 74b. Second opening 64 is preferably square shaped.

Aperture 60 is likewise configured by a plane, electrically conductive coating 78 on substrate 76. Coating 78, for avoiding eddy currents, is provided with a slot 80 extending away from first opening 62 to the periphery of coating 78. Preferably, first opening 62 is also square shaped.

Preferably, coatings 72 and 78 are provided with rounded corners.

The area ratio between first opening 62 and second opening 64, preferably, is in the range of between 1:2 and 1:6, still more preferably at about 1:4.

In a practical embodiment of the invention, designed for a radio frequency of 15 MHz, a length L of substrates 70 and 76 is, for example, 53 mm, and a width B is 19 mm. For this embodiment, first opening 62 has dimensions c×d of 2×2 mm, and second opening has dimensions a×b of 4×4 mm. Second opening 64, hence, is smaller as in prior art apparatuses according to FIG. 1 having no aperture, in which for the same frequency range the opening of radio frequency coil 22 is, for example 7×16 mm. The measuring depth, i.e. the distance from surface 38, at which NMR measurements are conducted, is about 2 mm for the above described embodiment of the invention.

Figure 5B:
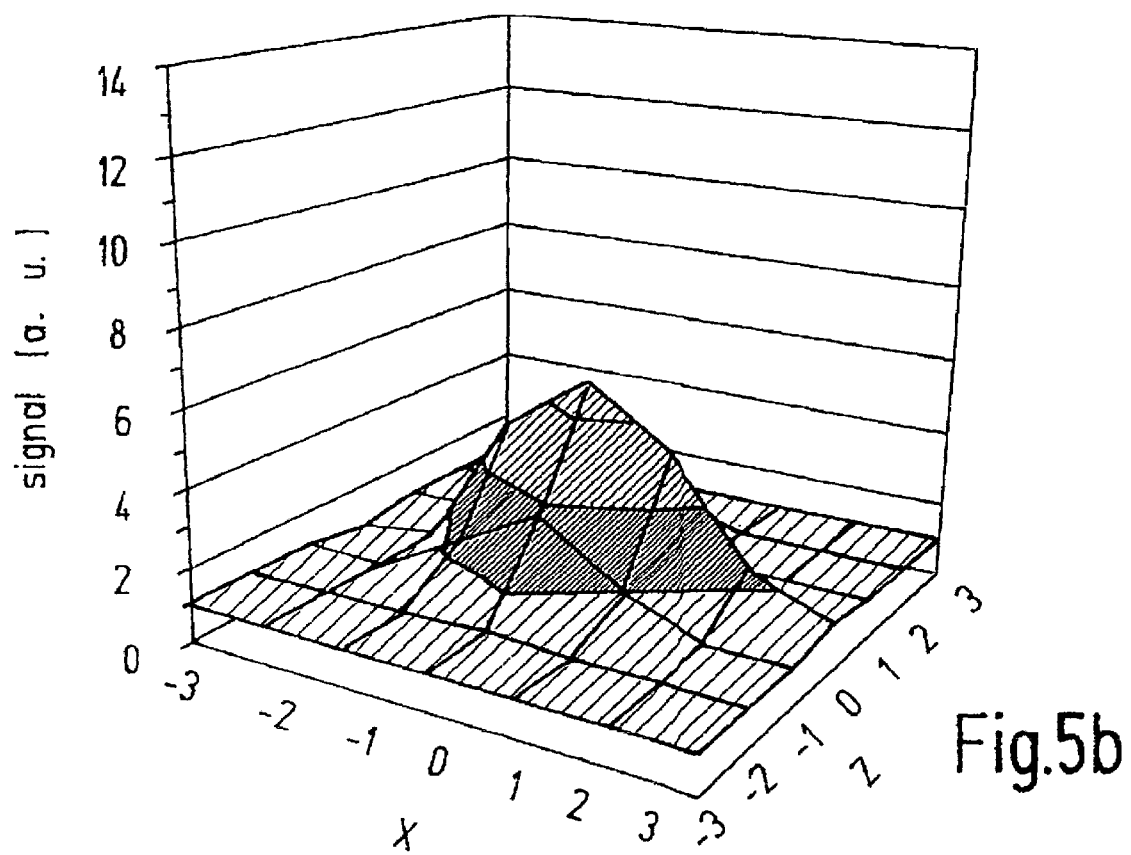
FIG. 5b, as an example, shows the experimentally determined two-dimensional spatial dependance of the measuring signal amplitude of a small sample object (1 mm³ natural caoutchouc) in a 1 mm raster within a plane directly at the surface without an aperture.

For the above described embodiment, FIG. 5, as an example, shows the experimentally determined two-dimensional spatial dependence of the measuring signal amplitude of a small sample object (1 mm³ natural caoutchouc) in a 1 mm raster within a plane directly at the surface: a) with aperture, and b) without aperture. As one can easily see, there is a considerable enhancement in signal amplitude in a) as compared to b), and an improved localization within the central area.

The NMR experiments were conducted in a manner as known per se, namely by using pulse sequences of field $B_1$.

What is claimed is:

1. A probe head for nuclear magnetic resonance measurements in an area of a measuring object surface, comprising a contact surface to be applied against said object surface, first means for generating a static magnetic field extending at least partially parallel to said object surface, a planar coil for generating a radio frequency magnetic field having components extending perpendicular to said object surface, and second means for concentrating a radio frequency magnetic field effective within said measuring object, said second means being configured as an aperture and being located between said planar coil and said contact surface.

2. The probe head of claim 1, wherein said aperture comprises a first opening, and a slot extending away from said first opening.

3. The probe head of claim 1, wherein said planar coil is configured as a loop-shaped conductive coating on a first substrate.

4. The probe head of claim 3, wherein said loop-shaped conductive coating is provided with a second opening being essentially square-shaped.

5. The probe head of claim 1, wherein said aperture is configured as a planar conductive coating on a second substrate, said coating being provided with a first opening.

6. The probe head of claim 5, wherein said first opening is essentially square-shaped.

7. The probe head of claim 5, wherein said planar coil is configured as a loop-shaped conductive coating provided with a second opening, wherein, further, said first and said second openings are arranged coaxially.

8. The probe head of claim 5, wherein said planar coil is configured as a loop-shaped conductive coating provided with a second opening, wherein, further, said first and said second opening have an area ratio in the range of between 1:2 and 1:6.

9. The probe head of claim 8, wherein said area ratio is about 1:4.

10. The probe head of claim 8, wherein when said radio frequency magnetic field has a frequency of about 15 MHz, said first opening has dimensions of 2×2 mm and said second opening has dimensions of 4×4 mm.

11. The probe head of claim 5, wherein said planar coil is configured as a loop-shaped conductive coating on a first substrate, said first substrate and said second substrate being configured as one same substrate, said planar coil and said aperture being located on opposite surfaces thereof.

12. The probe head of claim 1, wherein said first means are configured as a U-shaped magnet system, said second and said third means being located between legs of said U.

13. The probe head of claim 12, wherein said magnet system comprises two legs configured as permanent magnets interconnected by a yoke.

14. The probe head of claim 1, wherein said planar coil is located within an electrically conductive housing having a side facing said object surface, said second means being arranged within said side.

15. The probe head of claim 14, wherein means for matching and tuning said planar coil with respect to said radio frequency are provided within said housing.

16. The probe head of claim 14, wherein a plurality of exchangeable housings is provided, each housing having each said second planar coil and said third means.

* * * * *

UNITED STATES PATENT AND TRADEMARK OFFICE
CERTIFICATE OF CORRECTION

PATENT NO. : 7,271,589 B2
APPLICATION NO. : 11/440411
DATED : September 18, 2007
INVENTOR(S) : Roberto Melzi, Fabio Tedoldi and Giovanni Bizzaro It is certified that error appears in the above-identified patent and that said Letters Patent is hereby corrected as shown below:

Column 8,
Line 27, please delete "second".

Signed and Sealed this

Twenty-third Day of December, 2008

JON W. DUDAS
*Director of the United States Patent and Trademark Office*